(12) United States Patent
Lacey et al.

(10) Patent No.: US 6,943,009 B2
(45) Date of Patent: Sep. 13, 2005

(54) MULTI-WELL ASSEMBLY FOR GROWING CULTURES IN-VITRO

(75) Inventors: William J. Lacey, North Andover, MA (US); Gregory Mathus, Concord, MA (US); David M. Root, Westford, MA (US); John A. Ryan, Clinton, MA (US)

(73) Assignee: Corning Incorporated, Corning, NY (US)

( * ) Notice: Subject to any disclaimer, the term of this patent is extended or adjusted under 35 U.S.C. 154(b) by 297 days.

(21) Appl. No.: 10/146,831

(22) Filed: May 15, 2002

(65) Prior Publication Data

US 2003/0215940 A1 Nov. 20, 2003

(51) Int. Cl.⁷ .................................................. C12M 1/12
(52) U.S. Cl. ............................ 435/297.5; 435/305.2; 422/101; 422/102
(58) Field of Search ........................... 435/297.1, 297.2, 435/297.5, 288.1, 288.2, 288.3, 288.4, 304.2, 305.1–305.4; 422/101, 102; 210/474, 476, 482, 477

(56) References Cited

U.S. PATENT DOCUMENTS

| | | | |
|---|---|---|---|
| 4,871,674 A | 10/1989 | Matsui et al. ............... 435/284 |
| 5,026,649 A | 6/1991 | Lyman et al. ............... 435/284 |
| 5,141,718 A | 8/1992 | Clark ........................... 422/99 |
| 5,215,920 A | 6/1993 | Lyman et al. ............... 435/284 |
| 5,221,475 A | * 6/1993 | Mealey et al. .............. 210/474 |
| 5,466,602 A | 11/1995 | Lyman et al. ............. 435/297.1 |
| 5,468,638 A | 11/1995 | Barker et al. ............. 435/304.1 |
| 5,710,043 A | 1/1998 | Pay ........................... 435/297.5 |
| 5,766,937 A | 6/1998 | Lahm et al. ............. 435/297.5 |
| 5,795,775 A | 8/1998 | Lahm et al. ............. 435/297.5 |
| 5,801,055 A | * 9/1998 | Henderson ............... 435/297.5 |
| 5,922,289 A | 7/1999 | Wong .......................... 422/102 |
| 5,962,250 A | 10/1999 | Gavin .......................... 435/29 |
| 5,972,694 A | 10/1999 | Mathus .................... 435/288.4 |
| 6,043,027 A | 3/2000 | Selick et al. .................... 435/4 |
| 6,107,085 A | 8/2000 | Coughlin et al. ........ 435/299.1 |
| 6,146,883 A | 11/2000 | Grass ...................... 435/307.1 |

* cited by examiner

*Primary Examiner*—William H. Beisner
(74) *Attorney, Agent, or Firm*—Joanne N. Pappas

(57) ABSTRACT

A high-throughput cell or tissue culture apparatus, which is configurable to an industry-standard well plate format, is provided. The apparatus comprises a number of vessels, which may be suspended in wells of a plate. Each vessel has at least one sidewall defining a first opening and a second opening, each of predetermined cross-sectional area. The second opening has an inner cross-sectional area greater than either the inner cross-sectional area of the first opening or a cross-sectional area in a horizontal plane between the first and second openings. A relatively large substrate area is provided in each vessel for supporting tissue cultures in a fluid medium.

34 Claims, 18 Drawing Sheets

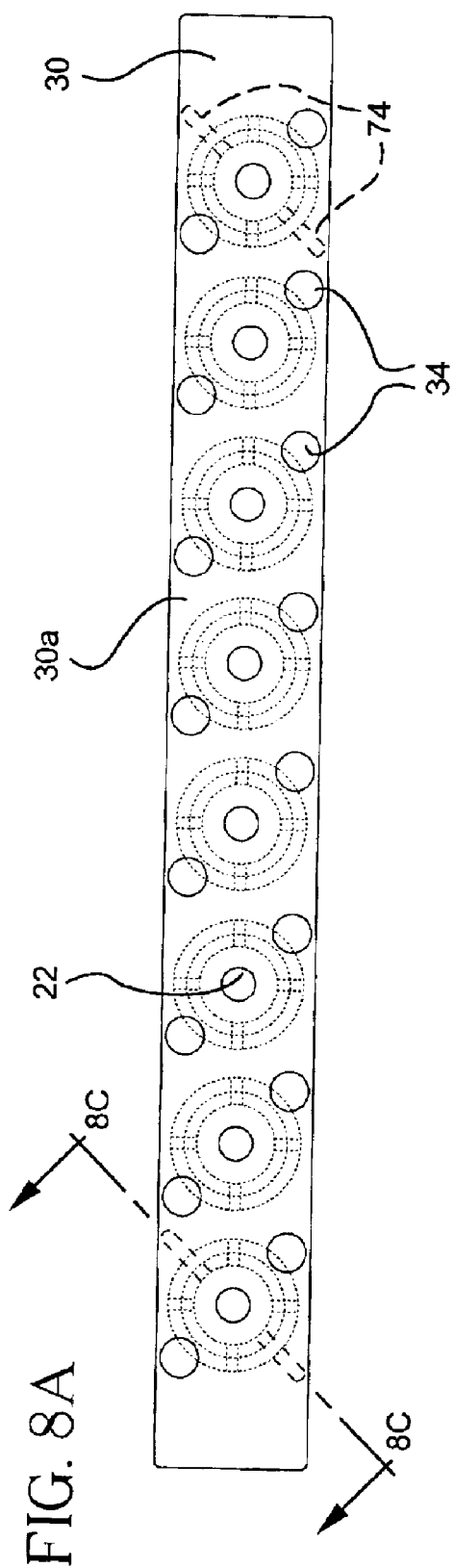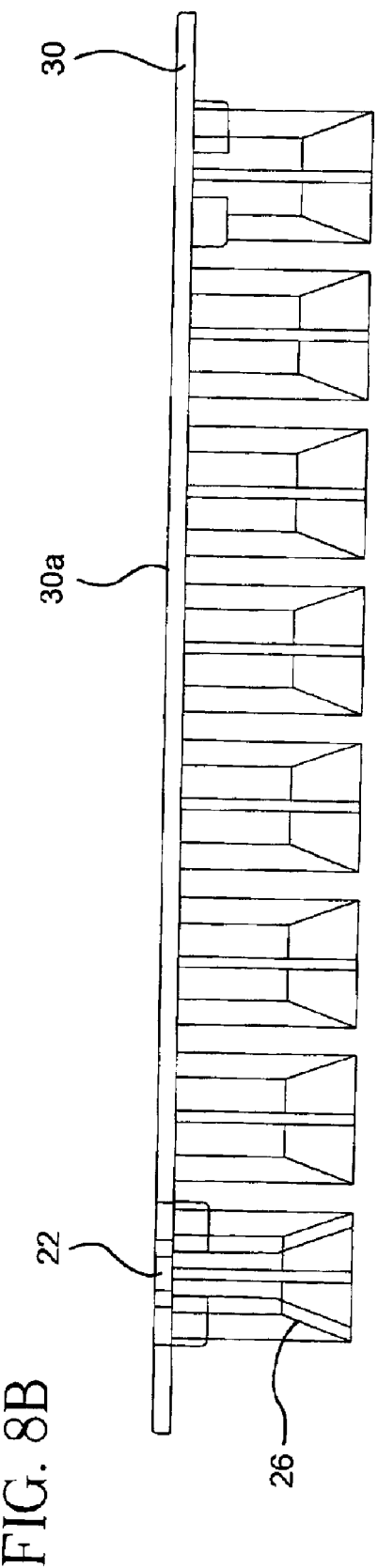
FIG. 8A
FIG. 8B

US 6,943,009 B2

MULTI-WELL ASSEMBLY FOR GROWING CULTURES IN-VITRO

TECHNICAL FIELD

The present invention pertains to an apparatus for growing cells or tissue cultures in vitro. More particularly, the present invention relates to a test plate apparatus that provides high-throughput capacity and large substrate area for supporting tissue cultures in a fluid medium. The apparatus also has apertures, which allow unfettered access to a well in a corresponding base plate below the culture substrate.

BACKGROUND

Cell or tissue sample growth in vitro, using a microporous membrane suspended in a nutrient rich culture medium, has several advantages. A cell layer may be seeded and grown relatively easily on the microporous membrane. The cells are fed through the membrane as a concentration gradient of nutrients develops between the two sides of the permeable membrane. This basolateral method of providing nutrients to cells more closely resembles the situation in vivo, where the plane of attachment of epithelial tissue to the underlying connective tissue is also the path of nutrient exchange. To scientists studying cellular transport and other biological activities, the creation of more naturalistic cellular conditions is an advantage.

To take advantage of the basolateral feeding method, cell culture inserts using a permeable membrane as culture substrate have been developed. The inserts fit into reservoirs or chambers of a culture plate, such that each membrane is immersed in the culture medium in a corresponding reservoir. Some devices include an opening that enables access to the culture medium below the permeable membrane. This access is essential for maintaining appropriate levels of nutrients and waste products in the culture medium. Through these openings, culture medium can be removed and replaced without disturbing the membrane substrate. Examples of some cell culture devices are described in U.S. Pat. Nos. 4,871,674, 5,026,649, 5,141,718, 5,215,920, 5,466,602, 5,468,638, 5,710,043, 5,962,250, and 5,972,694, the contents of which are incorporated herein by reference.

The pharmaceutical industry has for several years used inserts, such as shown in U.S. Pat. No. 5,026,649, in drug transport studies. Cells are grown to a confluent monolayer on a microporous membrane. Electrodes can be placed on either side of the membrane to measure the electrical resistance across the membrane so as to test the degree of confluency or integrity of the monolayer. Alternatively, optical detection of the leakage of a dye, such as Lucifer yellow, or radio-labeled solution, such as mannitol, from the insert chamber, across the cell monolayer, into the lower chamber, can provide confirmation of the degree of cell monolayer integrity. Once cell monolayer integrity is confirmed, a compound or solution to be tested is added into the insert chamber. After a suitable incubation period, one can assay for the test solution, in the chambers on either side of the membrane. The presence and concentration of the compound in the lower chamber indicates the ability of the compound to be transported though the particular cells comprising the monolayer. As the drug discovery process provides more new compounds for testing, the need for culture arrays with more dense configurations capable of performing cell transport studies in high-throughput on an industrial scale for the screening of large numbers of drugs have become apparent. Culture devices available at the present time, with adequate membrane surface, include a 6.5 mm diameter membrane insert loaded in a 24 well cluster plate. This design unfortunately does not fit the standard industry format.

The industry-standard microplates are typically configured with 96 wells. The wells in a 96-well plate each has an appropriate cross-sectional area of about 0.053 square inches, and are arrayed in an 8×12 matrix (e.g., mutually perpendicular 8 and 12 rows) with a spacing of about 0.354 inches (~9 mm) between the centerlines of rows, both in the x and y directions. In addition, the height, length and width of the 96-well plates are standardized. Standardization has given rise to a large assortment of auxiliary equipment developed to use the 96-well format. The equipment includes devices that load and unload precise volumes of liquid in multiples of 8, 12, or 96 wells simultaneously. Other equipment read calorimetric, fluorescent or luminescent changes in the solutions in individual wells. Further, some of the equipment involves robotic automated handing systems, which are instrumented to record, analyze, and manipulate the data recorded.

U.S. Pat. No. 5,141,718 (Clark) discloses an apparatus that combines a strip insert with a plate containing tear-shaped reservoirs. Each reservoir is comprised of circular portion and a triangular portion. The strips are comprised of a plurality of tubular members attached to membranes. These strips are inserted into the plate such that each tubular member is immersed in a reservoir. The tubular member occupies substantially the entire circular portion of the reservoir. Access to the reservoir is attained through the triangular portion, without disturbing the membrane substrate. The problem with this apparatus design is twofold. First, the wells are not adaptable to an industry standard 96-well format, thus they are not adaptable to much of the auxiliary equipment designed specifically to handle such plates. Second, the parallel sides of the tubular members, when placed close to the sidewalls of the reservoirs will tend to trap the liquid medium in between, which can lead to capillary action. The fluid in the narrow space has a tendency to wick up the sides to the top surface of the plate and cross-contaminate neighboring wells. To present this phenomenon, an insert with a smaller diameter is used. This solution, however, sacrifices the total amount of membrane surface area available.

Over the years, others have attempted to construct tubular, membrane insert devices in a standard 96-well format, but have been without noticeable success. An insert device suspends a membrane within a well. To suspend the membrane without touching the walls of the reservoir well, the membrane itself must be substantially smaller in diameter than the interior diameter of the reservoir well. Further, access to the lower part of the well is accomplished usually by inserting a pipette tip or syringe to the side of the suspended membrane. Therefore, the suspended membrane must be not only small enough to prevent contact with the well of the well, but also small enough to allow a pipette tip or syringe to fit between it and the wall of the well. Typically, a circular well in a 96-well format plate has a relatively small diameter (e.g., ~0.267–0.325 inches). Tubular membrane inserts that fit within these small wells have membranes that are considerably smaller in diameter (e.g., ~0.120 inches) than the wells. These small membranes are difficult to handle and perform studies upon. Moreover, in a 96-well format, the small diameters prohibit the building of a device with adequate membrane surface area.

In response to the shortcomings of the apparatus shown in the Clark patent, a plate that has a standard configuration and integrated construction was developed. U.S. Pat. No. 5,972,694 (Mathus) discloses a micro-titer well plate, wherein each well of the plate has an upper chamber and a lower chamber separated by a microporous membrane. Adjacent to each well is a corresponding access port. The access port is a separate opening in the top surface of the plate, which provides direct access to the lower chamber of the corresponding well without disturbing the upper chamber or the membrane. The problem with this design is also a danger of cross-contamination or cross-talk between the individual wells caused by the mingling of fluids. When a unitary microporous membrane is sandwiched between the upper and lower portions of the plate, as is the case in this device, liquid from one well may wick through adjourning portions of the membrane. Soluble molecules, such as test drug specimens, cell products, or waste, can seep into adjacent wells, thereby contaminating the culture samples contained in neighboring wells. Cross-talk can is considered highly undesirable inasmuch as it serves as a source of contamination, interferes with the accuracy of an assay, or causes ambiguity in results.

The present invention solves these various problems linked with attempts to miniaturize membrane inserts to fit the 96-well format. The culture apparatus according to the present invention has a new shape and well structure, which virtually eliminates capillary action or backwash and reduces the possibility of fluidic cross-talk. According to the present invention, the design also maximizes the interior diameter of each well in a base plate. Each well in the plate shares a common sidewall with at least one other well. The sidewall of each well should be kept to a minimal thickness. The space-savings associated with two adjourning wells sharing a common solid sidewall can be substantial—enough to increase the overall available membrane surface area of the plate by at least a factor of three.

SUMMARY OF THE INVENTION

The present invention provides a high-throughput cell or tissue culture apparatus that is configurable to an industry-standard well plate format. The apparatus may be employed in a variety of uses, such as for cancer or pharmaceutical research. The apparatus includes a number of "vessels," "insert-articles," or "upper chambers," which may be suspended in a number of lower chambers, reservoirs, or wells in a base plate. The vessel has at least one sidewall defining a top or first opening and bottom or second opening, each of predetermined cross-sectional area. The sidewall of the vessel is shaped, having at least a portion that is sloped or flared laterally, extending downward and outward, creating an inverted draft with, preferably, a larger bottom opening than top opening. As expected, the inner cross-sectional area of the insert bottom opening is greater than the inner cross-sectional area of the insert top opening or any parallel plane in between. A permeable or microporous membrane for depositing samples extends across the bottom opening of each vessel. Once enclosed, the vessels alternatively may be called "culture vessels." The apparatus may also include a base or lower plate. Each well in the base plate has a bottom wall and at least one sidewall. The sidewall having a top edge surface, and when the number of wells exceeds one, adjacent wells share a common sidewall.

A virtue of the present invention is in the shape of the vessel. Generally, the vessels have a cross-sectional area between the first and second openings, in a horizontal plane orthogonal to a sidewall of a well, which is smaller than the inner cross-sectional area of the second opening. The vessels will preferably take on the shape of a frustum, sized to fit into a tubular-shaped well having largely parallel sides. Other shapes, such as like an hourglass, are also possible. The vessel or insert-article not only decreases the adverse effects of capillary action, but also maximizes the cross-sectional or surface area of substrate membrane available for deposition of culture samples. As more fluid media is introduced into each well of the base plate the fluid level rises, potentially creating a backwash problem when a vessel is inserted. The distance between the wall of the well and the side of the vessel widens for a greater amount of available space. This decreases the chance for capillary action or cross-talk.

In conjunction with the vessels, the present invention also includes a redesigned base plate. The wells in this plate have a larger cross-section or diameter than a standard well. This feature permits one to use a substrate membrane with a diameter that is the same or larger than that permitted by the constraints of standard-sized wells in a 96-well plate, while still maintaining the standard format. This represents an increase in the average amount of membrane surface area of about 3–5 times over that used in comparable devices. Moreover, a greater volume of fluid media can be introduced into each well than currently possible in standard 96-well plates. Alternatively, a 384-well plate of standard footprint, according to this aspect of the invention, may achieve a membrane surface area comparable or equal to a conventional 96-well plate.

According to some embodiments, a horizontal surface or flange extends from the top opening of the vessel. This flange is an integral structural element that may support and join together individual insert-articles when fabricating interconnected units, either in the form of a linear strip or x-y oriented matrix of culture vessels, for example a 24-, 48-, 192-, 384-, or 1536-well design. At least one aperture formed as part of the horizontal flange provides access to the contents in a corresponding well of the base plate. A raised collar-lip surrounds the top opening of each of the vessels to prevent potential leakage or other cross contamination between inserts when fluids are introduced.

In another aspect, the present invention also includes a method of manufacturing an insert-article for a multi-well cluster plate. Insert-articles can be molded without resorting to using side action, as is common in the molding art to make hour-glass shaped pieces. A matrix of multiple insert-articles can be fabricated in one step according to an embodiment of the method, thereby providing both savings in manufacturing cost and processing-assembly time. The method includes providing a mold having a first component with a bottom and a central core pin and at least one peripheral component which defines a mold cavity having a sloping sidewall. The first component has a portion with narrowing diameter from the bottom, which extends for at least part of the length of said central core pin. Assembling the mold, such that the peripheral component encloses the central core pin of the first component, and introducing a formable material is into the mold. An insert-article with a central cavity, defined by a sidewall, extending from a first open end to a second open end is then removed. The second open end has an inner cross-sectional area greater than the inner cross-sectional area of the first open end or a cross-sectional area in a horizontal plane between the first and second open ends, such that at least a part of said insert-article has a flared shape. Lastly, a permeable substrate suitable for sustaining culture samples is attached cross the second open end. The peripheral mold component and the central core pin engage each other respectively from above and below to avoid side-action.

Additional features and advantages of the present invention will be set forth in the detailed description that follows. It is to be understood that both the foregoing general discussion and the following detailed description and examples are merely representative of the invention, and are intended to provide an overview or framework for understanding the invention as claimed.

BRIEF DESCRIPTION OF FIGURES

FIGS. 8A, 8B, and 8C, respectively, depict another eight-vessel strip in top and side views, and enlarged cross-sectional view along the line 8C—8C of one of the vessels according to an embodiment of the present invention.

FIG. 10A represents a top plan view of a fragment of a 96-well base plate with circular wells, according to the present invention, whereby the sidewall of each well overlaps tangentially another. FIG. 10B represents a top view of a fragment of a base plate with paddle-shaped wells, whereby each well shares a common sidewall with another well.

DETAILED DESCRIPTION OF THE INVENTION

Figure 1:
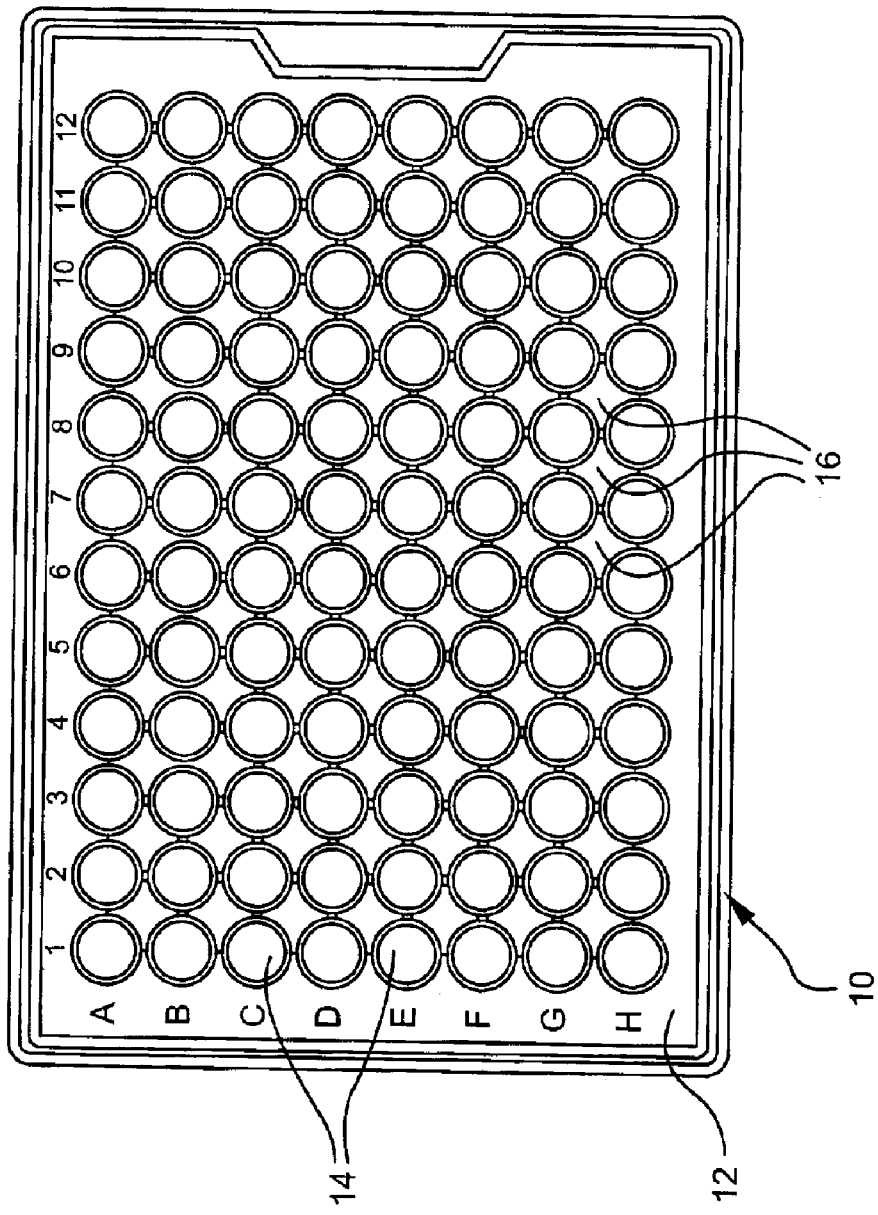
FIG. 1 is top plan view of a 96-well cluster plate with its wells and overall dimensions conforming to the standardized format adopted by industry.
Figure 1A:
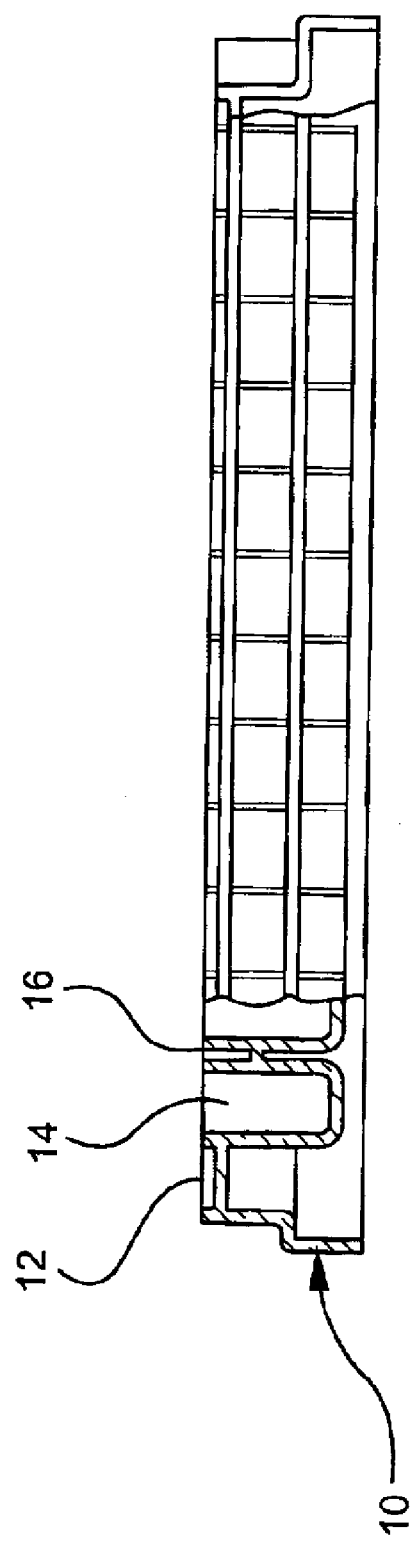
FIG. 1A is a side view of the 96-well plate shown in FIG. 1 with part of the peripheral skirt cut away.

FIGS. 1 and 1A show a 96-well plate that exemplifies the general configuration of the current industry-standard format. Its overall height, width, and length are standardized at ~0.560, 3.365, and 5.030 inches, respectively. The plate includes a surrounding skirt 10, a top surface 12 and an array of wells 14 arranged in twelve rows of eight wells each, to provide 96 identical wells in the plate. The top surface 12 extends between the skirt and the periphery of the wells on the outside of the 96 well matrix. The plates typically are molded of plastics and are provided with transparent covers (not shown) with drop rings to control water loss by evaporation, while allowing gas exchange and maintaining sterility As discussed above, standardization of the 96-well format has led to the development of a substantial variety of equipment to perform liquid transfers to and from the well chambers, to transmit light through the wells, to read colorimetric or fluorescent changes, or chemiluminescence in individual wells, and many other functions. The liquid transferring equipment is either manually or robotically operated, and much of the equipment used to study the contents of wells is automated and instrumented to record, analyze and manipulate the data. The present invention provides automation-friendly vessels and either a single reservoir or a multi-well base plate that is compatible with the auxiliary equipment designed for the 96- or 384-well format in all aspects.

Figure 2A:
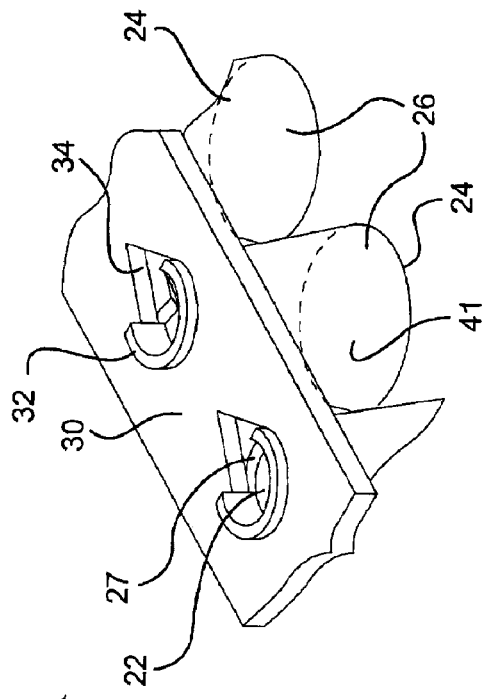
FIGS. 2A and 2B illustrate variations on the vessel design of FIG. 2.
Figure 2B:
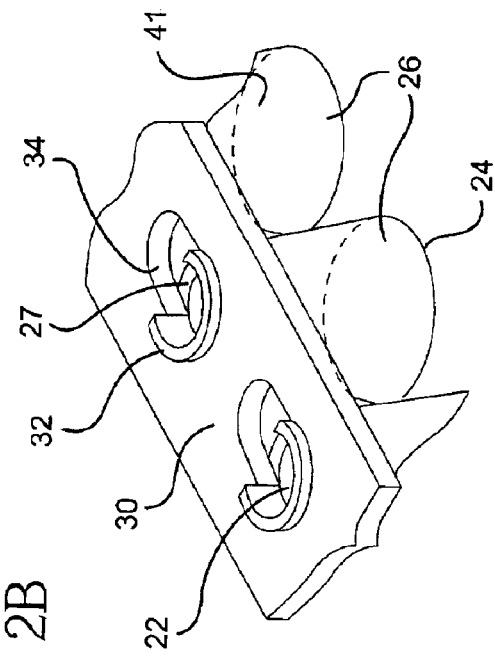
Figure 2:
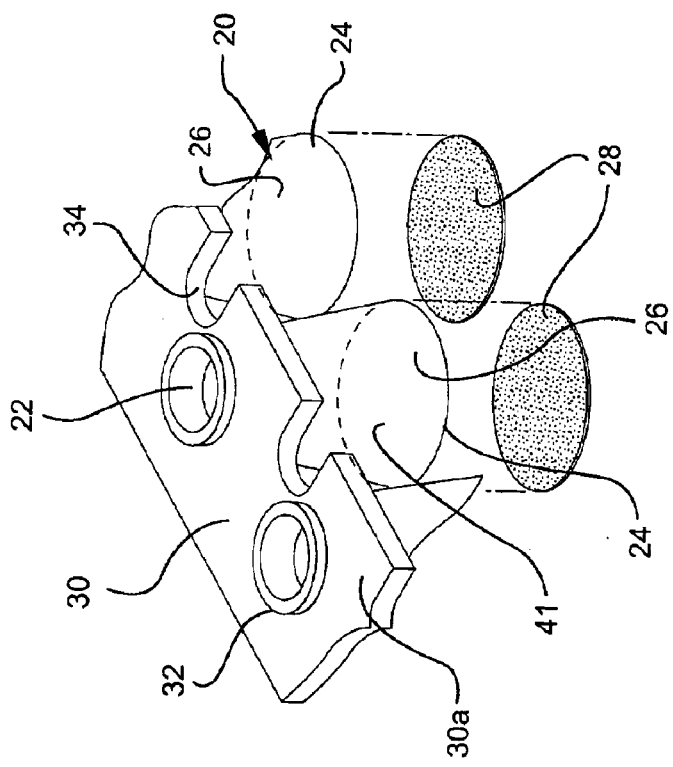
FIG. 2 shows an exploded view of a vessel with a substrate membrane—also called an insert-article.

To describe and illustrate more clearly the present invention, the following embodiments and examples are provided in detail, which however are not intended to be limiting of the invention. FIG. 2 shows an exploded view of an embodiment of an insert-article or culture vessel 20, which constitutes a basic unit of the present invention. The vessel is made up of several structural elements. The vessel has a first or top 22 and second or bottom opening 24 defined by an outwardly spreading or flared external surface(s) or sidewall(s) 26. The top opening 22 of the vessel is smaller than the bottom opening 24. In preferred embodiments, the insert is in a frusto-conical, stepped-frusto-conical, or frusto-pyramidal shape, which is likened to the form of a miniature Erlenmeyer flask. The ratio of the size of the first opening, or a cross-sectional area of a horizontal plane parallel the bottom wall of a well, to the second opening preferably should not exceed about 98.8%. To the larger bottom opening 24 a permeable membrane 28 for the deposition of cells or tissue samples is attached by various methods (e.g., heat-sealing, laser or ultrasonic welding, solvent or adhesive bonding). From about the top opening 22 extends a horizontal surface or flange 30 having a top surface. Depending on the specific embodiment, this horizontal surface may be a structure that joins together individual vessels into a strip of multiple vessels, or may be extended to become the top surface of a x-y oriented matrix of 96-inserts for a corresponding plate. To prevent errant drops of liquids or other contaminants, which may be on the horizontal surface 30 from falling into a vessel 20, a raised lip 32 is formed around the vessel's top opening 22. In an example, the collar-lip 32 rises up about 0.020 inches above the horizontal flange at the top opening.

Figure 3A:
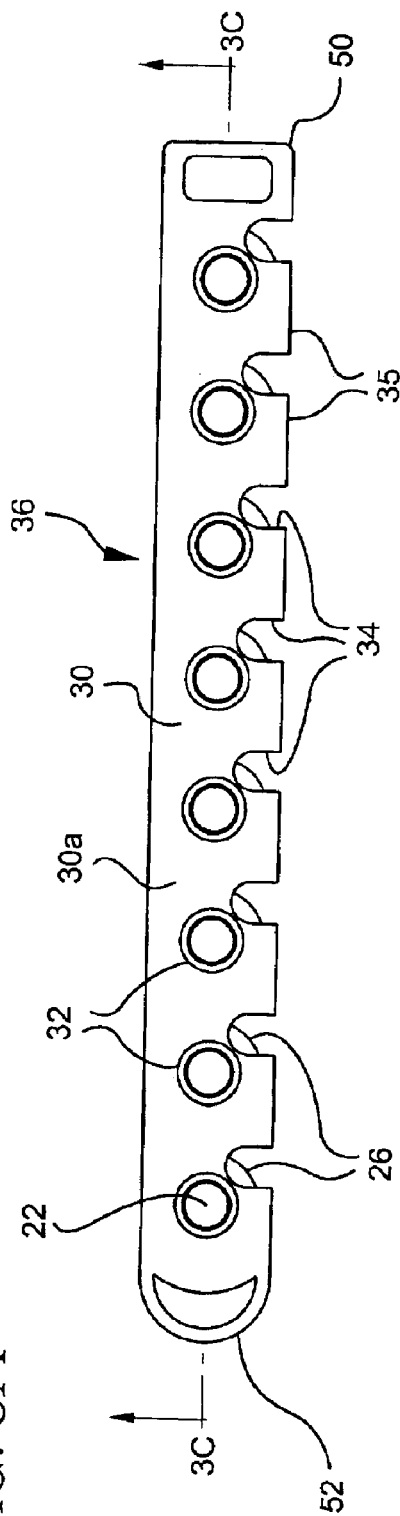
FIGS. 3A, 3B, and 3C, respectively, depict three views: top, side and cross-section along the longitudinal centerline of an eight-vessel strip according to the present invention.
Figure 3B:
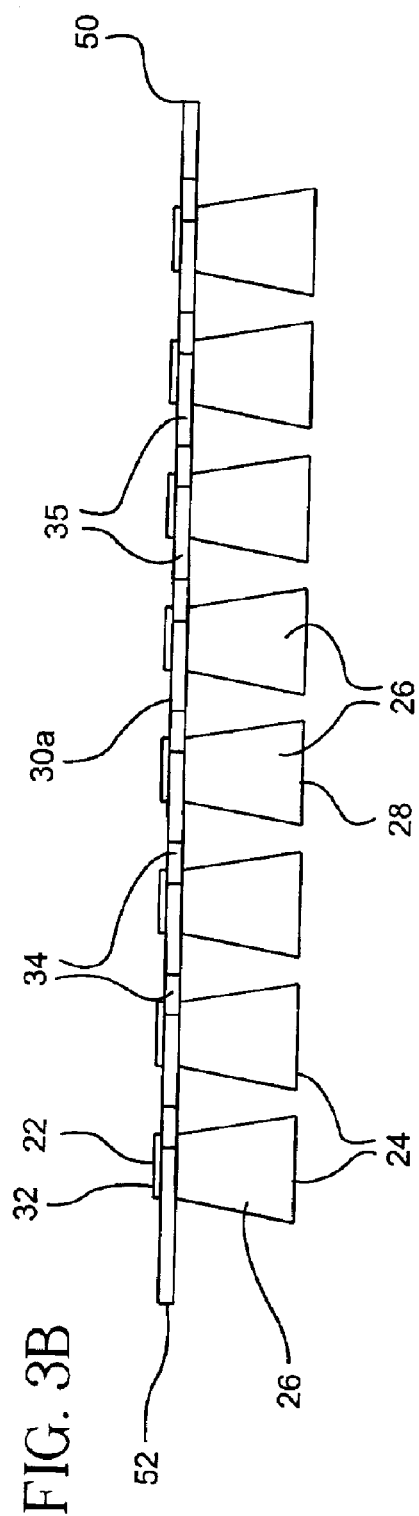
Figure 3C:
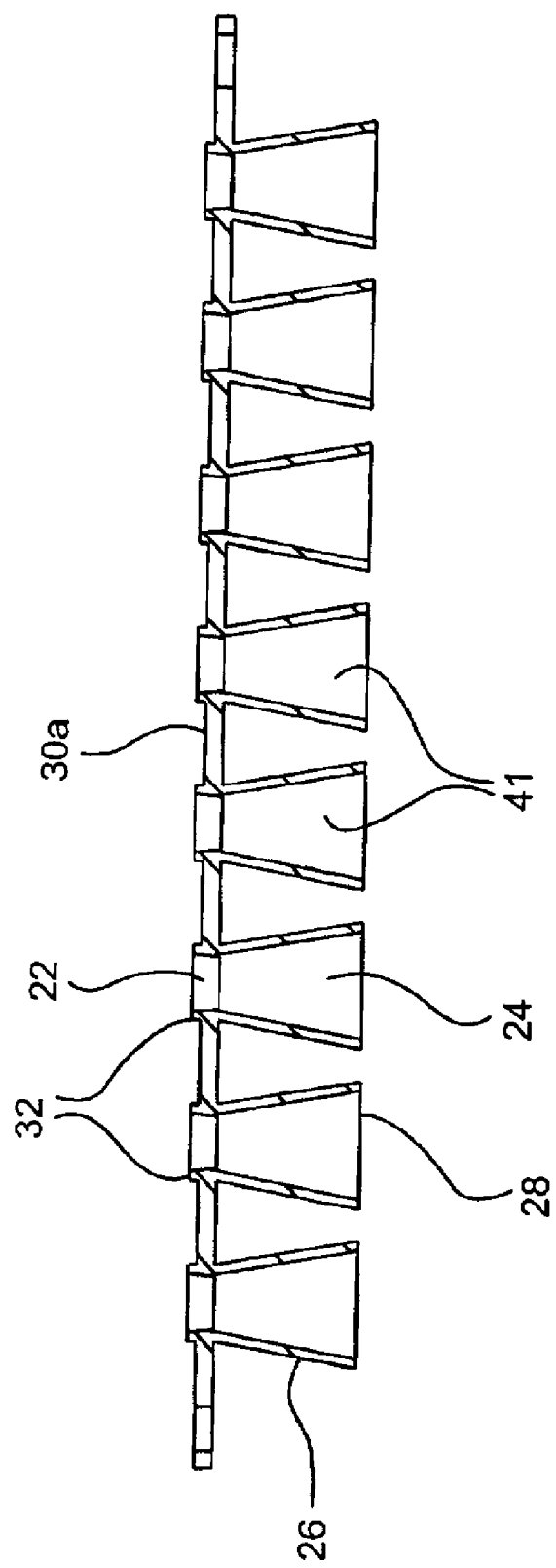
Figure 4A:
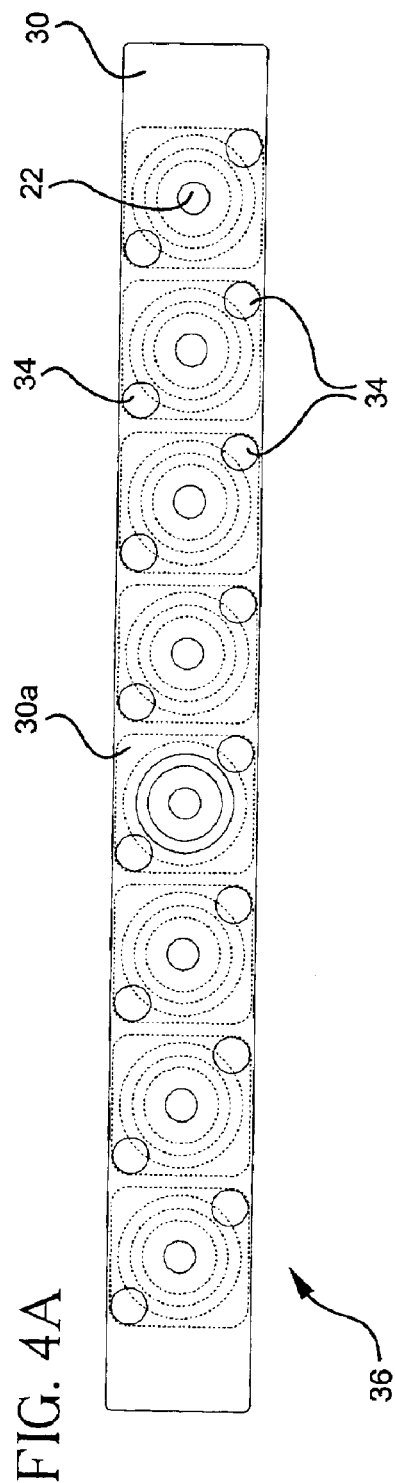
FIGS. 4A, 4B, and 4C, respectively, depict another eight-vessel strip with two access ports, in top and side views, and enlarged cross-sectional view of one of the vessels according to an embodiment of the present invention.
Figure 4B:
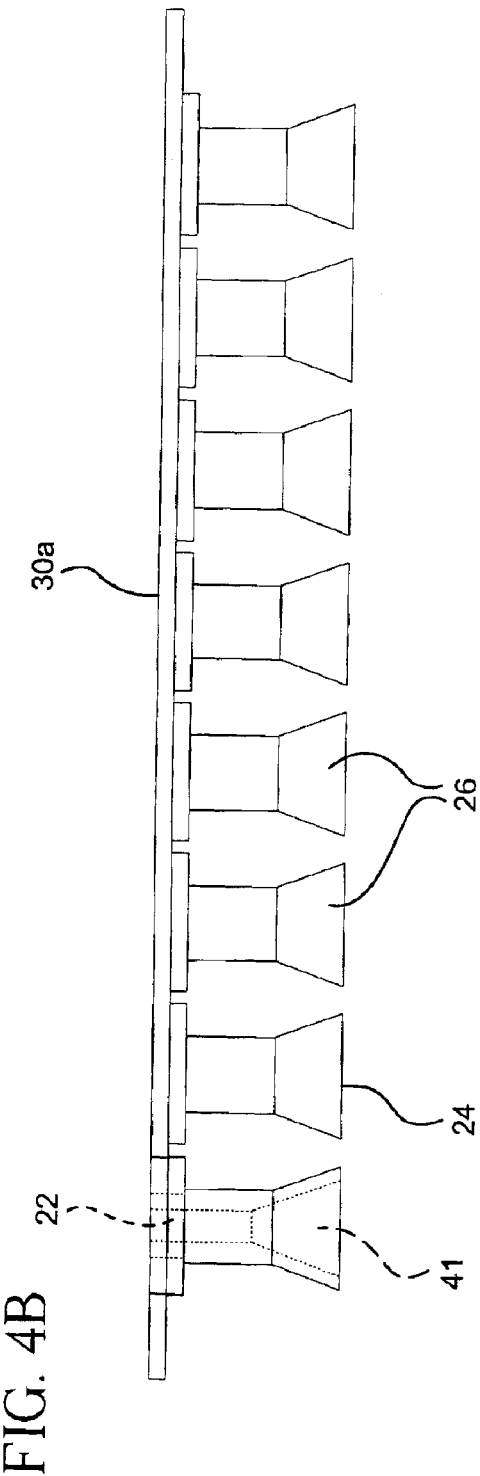
Figure 4C:
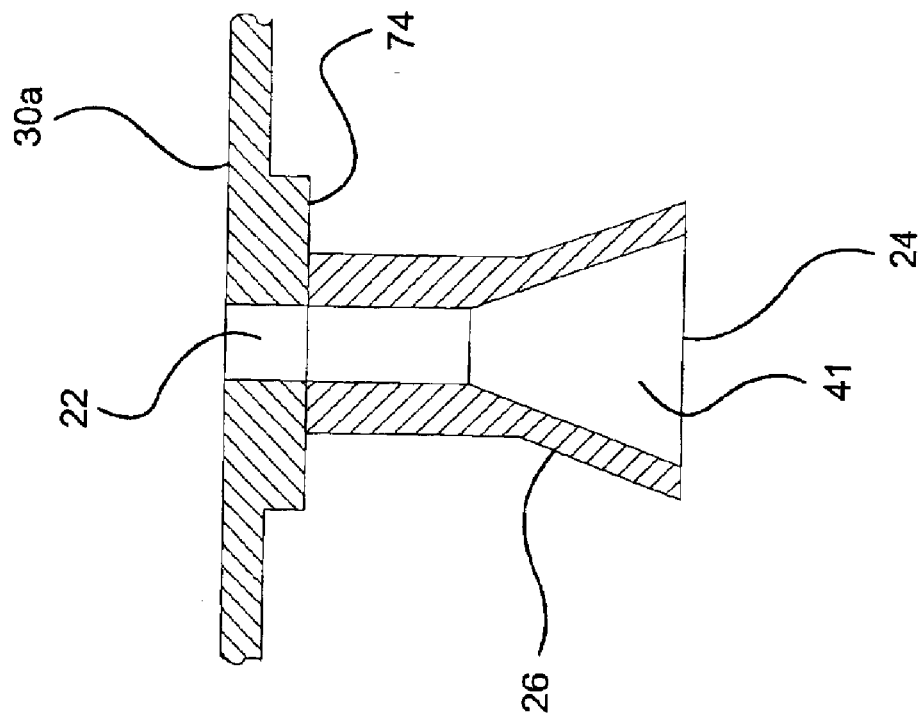

Next to each vessel, an access portal or aperture 34 is located in the horizontal surface 30 for communicating with a well when the vessel is suspended in a base plate. In an embodiment, the aperture 34 may be part of the top opening 22, to create a single larger opening in a lozenge or tear shape, as depicted in FIGS. 2A and 2B. When the aperture 34 and top opening 22 form a single large opening, the sidewall 26 adjacent to the aperture 34 may have a notch or recess 27, through which an instrument (e.g., pipette, luer, or syringe) may alternatively access both the interior of the vessel and the chamber below, without withdrawing fully from either. At least a portion of the sidewall 26 of the vessel and, in some embodiments the top surface of the horizontal flange 30a, separates the access aperture 34 from the interior cavity 41 of the vessel, which reduces the chance of disturbing the membrane substrate 28. The specific location of access apertures is not critical, so long as each vessel has at least one associated access portal. In some embodiments, like that of a strip 36, access apertures 34 are provided along an external, longitudinal edge 35 of the horizontal flange 30, like in FIGS. 3A, 3B and 3C. In other examples, two or more access apertures are provided such as illustrated in FIGS. 4A, 4B, and 4C. Through the access aperture 34 media and drug compounds may be tested or exchanged without disturbing the membrane substrate 28.

Figure 5B:
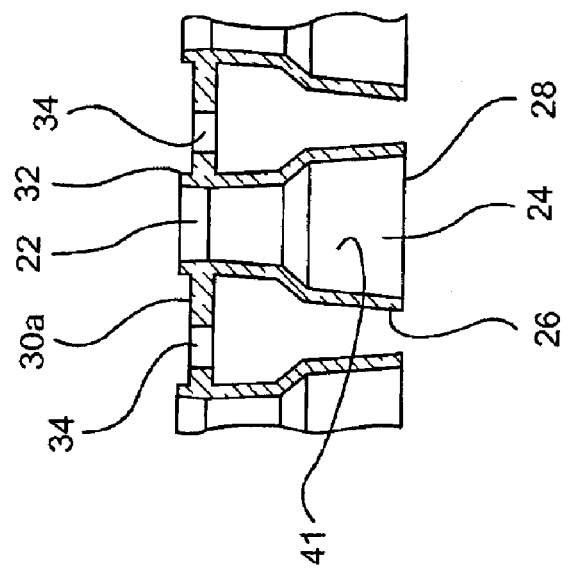
FIGS. 5A and 5B, respectively, show in three-dimensions and cross-section a vessel according to a so-called "step-design."
Figure 5A:
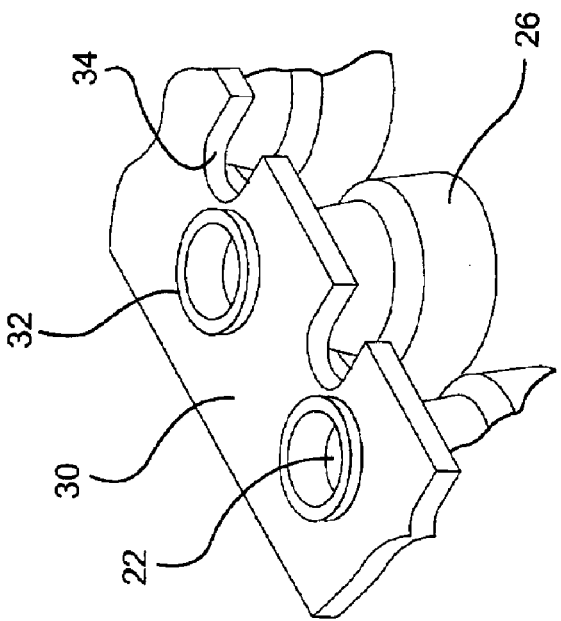
Figure 5D:
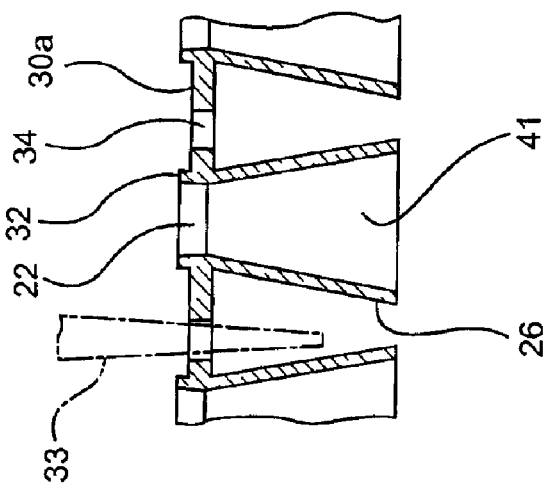
FIGS. 5C and 5D, respectively, show in three-dimensions and cross-section a vessel having an enlarged capacity for membrane surface area.
Figure 5C:
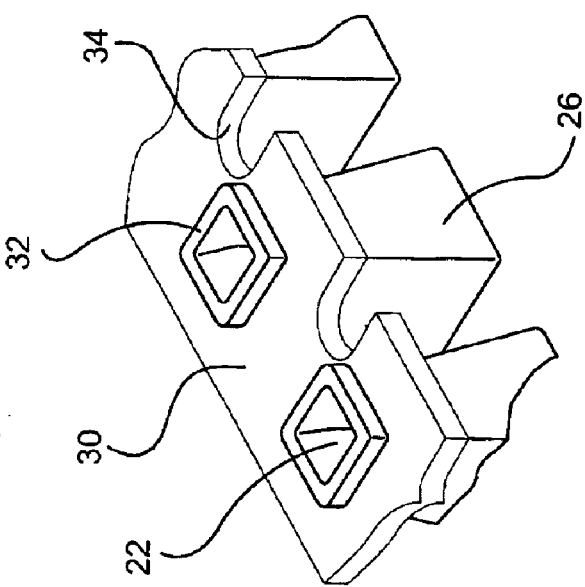

As discussed above, each vessel, in preferred embodiments, has a sloped sidewall 26 extending downward and outward from top openings 22 to form a greater cross-sectional area at the bottom 24 of each insert than at the top, creating an insert with an inverted-draft relative to conventional inserts. The vessels can have a variety of shapes, included a so-called "step design," shown in FIG. 5A in perspective. FIG. 5B depicts a cross-sectional view of this embodiment. Like other iterations of the insert design, the sidewall of a "step design" insert descends from a top opening 22 (e.g., ~+2 degrees/side). At about halfway down the side of the vessel, however, the sidewall projects outwardly at an angle of about 1–45° relative to the horizontal bottom of the insert, creating a step 29 or jog in the profile. At a predetermined distance (e.g., ~0.140 inches) from the bottom of the insert-article the sidewall resumes the slope it had above the step 29. FIG. 5C shows another preferred embodiment, which can maximizes the available membrane surface area. A two-dimensional, cross-sectional view of this embodiment is represented in FIG. 5D, which shows either a pipette tip or syringe 33 being inserted through the access aperture 34. The sidewall 26 of the insert descends from the top opening 22 and provides a bottom with a cross-section of ~0.30 inches. Some specific examples of insert-articles may have a draft of about 0.36–0.40 inches.

Figure 6B:
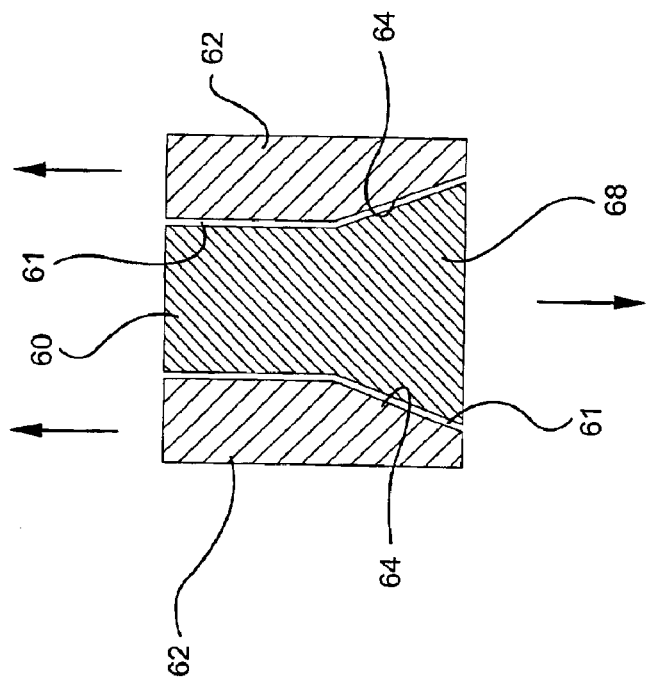
FIG. 6B shows a two-dimensional cross-section of the mold depicted in FIG. 6A.
Figure 6A:
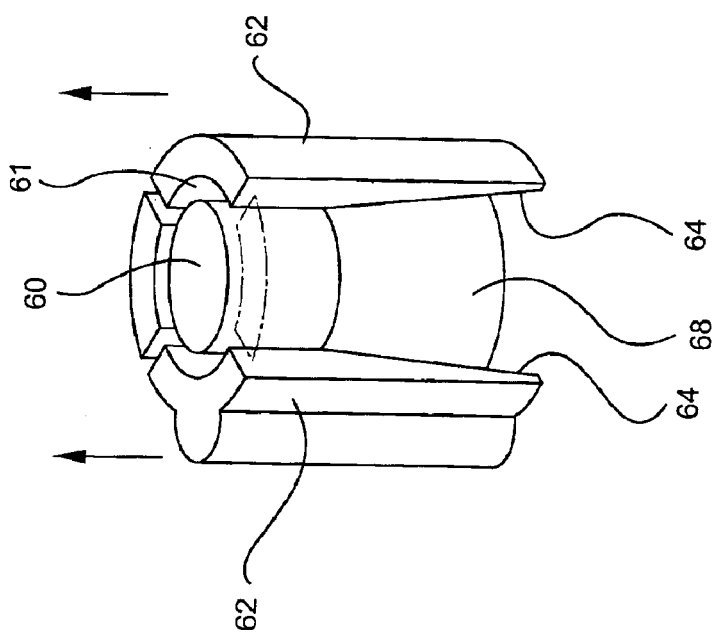
FIG. 6A shows a perspective view of components of a single unit, with a quarter cut away, of a mold for making the insert-articles according to a method of the present invention.

A vessel or insert-article can be molded as a unitary, integral body of plastic from any standard polymer material available in powdered form (e.g., polystyrene, polypropylene, polycarbonates, polysulfones, polyesters or cyclic olefins) using injection molding methods. According to the present invention, a method for manufacturing an insert-article for a multi-well cluster plate comprises, in part, providing a mold having a first component with a central core pin 60 and at least one peripheral component 62, which define a mold cavity 61 having a sloping sidewall 64. FIG. 6A depicts a partial cut-away view in three-dimensions of these components in relation to each other. FIG. 6B shows the same in two dimensions. The central core pin 60 is characterized by a flared portion 68 that extends for at least part of the length of the pin 60. The flared portion has either a circular or rectilinear lateral cross-section. Assemble the mold, such that the peripheral component 62 encloses the central core pin 60, and introduce a formable material into the mold cavity 61. After the material sets, remove from the mold an insert-article. As described above, the insert-article has a central cavity defined by a sidewall, which extends from a top open end to a bottom open end, creating a flared shape. Attach cross the bottom open end a permeable substrate suitable for sustaining culture samples. The substrate may be of similar or a dissimilar material to that of the body of the insert-article, and preferably the substrate is an organic membrane.

Figure 7A:
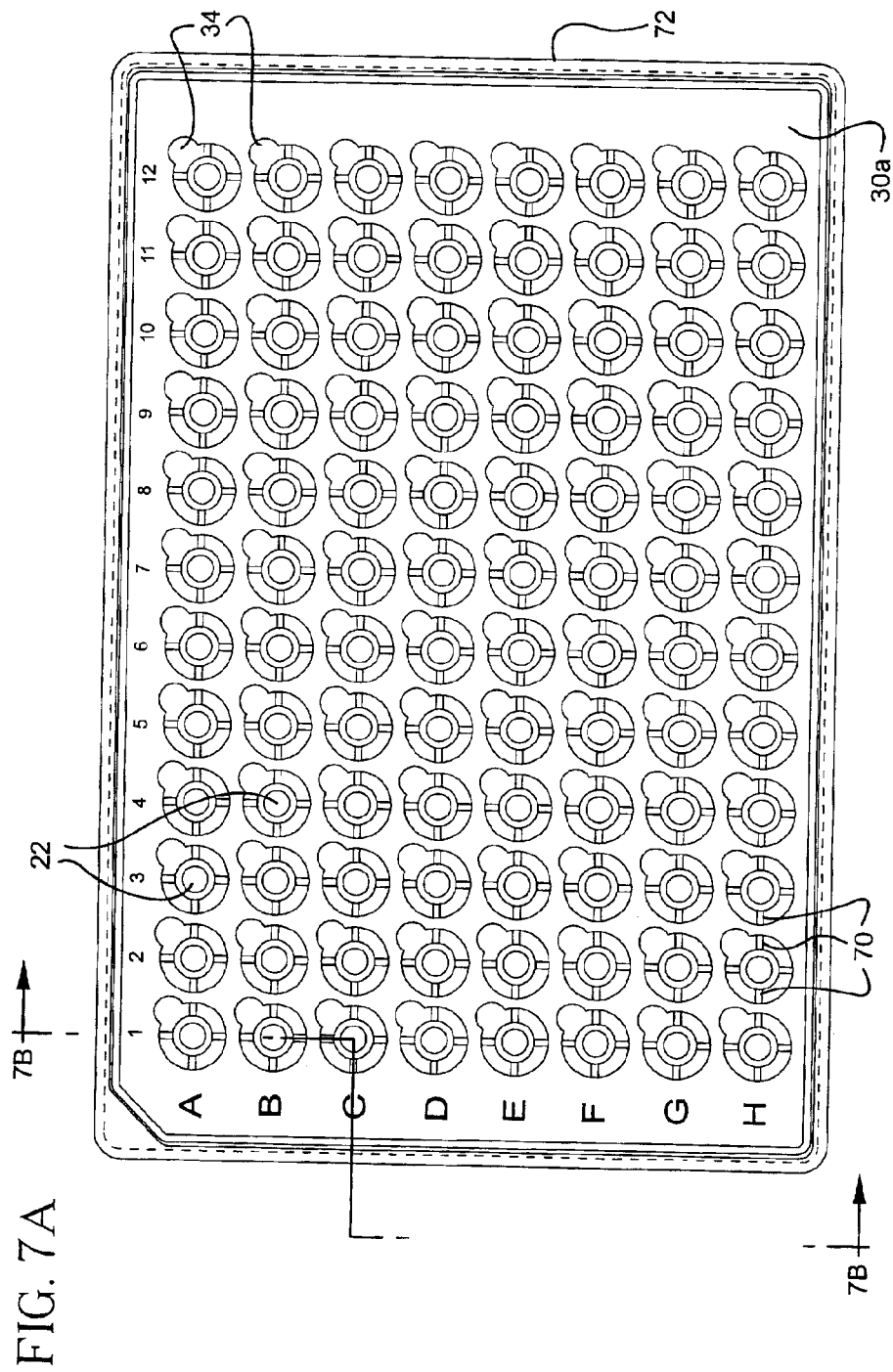
FIGS. 7A and 7B, respectively, shows a top plan and partially cut-away side view along of a vessel plate having a 96-well format, wherein according to an embodiment, the vessels and top flange surface are integrally molded as a single piece.

According to conventional injection molding techniques, the ways to mold an hour-glass-shaped form are limited. To accomplish this feat for the present insert-articles, undercut sides are required to provide for a horizontal flange extending from an upper portion of the insert-article with a lower portion that is of the same or larger size. For the components of the mold to be easily withdrawn from around the frustum shape, the insert-articles conventionally must be made either individually or in a single line since side action is required to remove the mold components. The present invention includes a design and method of manufacture, whereby the peripheral mold components mate vertically with the central core pin to avoid side-action. In other words, peripheral component(s) 62 is introduced vertically, from above or below, as the case may warrant, around the central core pin of the first component 60 to encase the central core pin. When one disassembles the mold, the first and peripheral components are withdrawn in opposite directions relative to each other. As illustrated in FIGS. 6A and 6B, the vertical arrows pointing up and down represent movement for each constituent part when the mold is separated. The advantage of this technique is that entire x-y oriented matrices of insert-articles, like that shown in FIGS. 7A and 7B, may be made in one step. Once the peripheral components are withdrawn through the top flange 30a, the holes that remains can serve as access apertures 34, as shown in detail in FIG. 7A. The pieces of molding between the peripheral component(s) act as ribs 70 to stabilize each insert-article. Previously in an alternate embodiment, the mold components mate laterally, from either side, with the central core pin. Several multi-insert strip are formed and then welded together to form, for instance, a 96-well matrix. This, however, is at least a two-step fabrication process and rather inefficient.

Figure 7B:
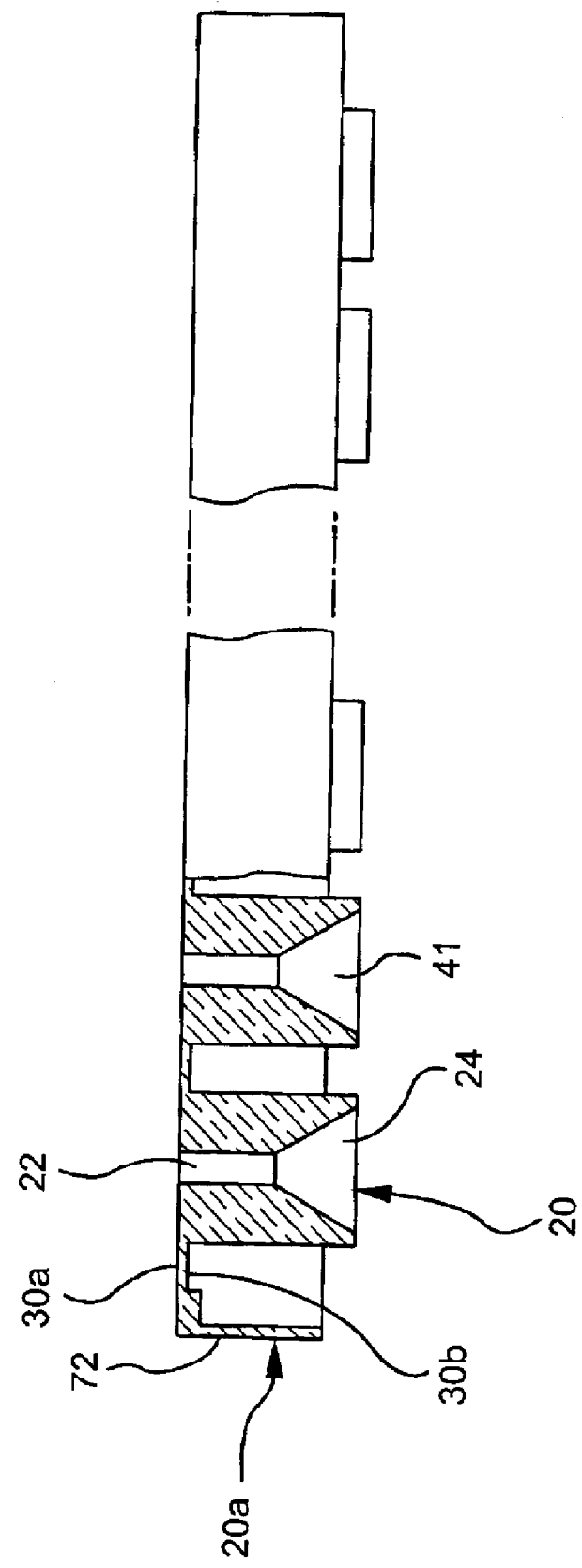

As a broad concept, the insert-articles may be individual pieces of various sizes, not limited necessarily to the size of a standard or even slightly enlarged well, so long as the general precepts of the insert are preserved. More practical for high-throughput purposes, however, the insert-articles may be arranged in strips of eight or twelve, like that shown in FIGS. 3 and 4, or as a matrix of insert-articles of any configuration, including a 48-well or the standard 96-well format, like that shown in FIG. 7A. FIG. 7B depicts a cut-away side view of an insert-article plate 20a formed like a cover for a 96-well plate. The horizontal flange 30 from each insert-article joins together to form the top surface 30a of the insert-article plate. Insert-articles 20 project down from its bottom surface 30b. A peripheral skirt 72, which serves both to protect the insert-articles 20 and as a means for easier handling and engagement, extends downward from the horizontal flange 30. Once aligned, the entire 96-insert plate can be easily introduced into a corresponding base plate.

Figure 8C:
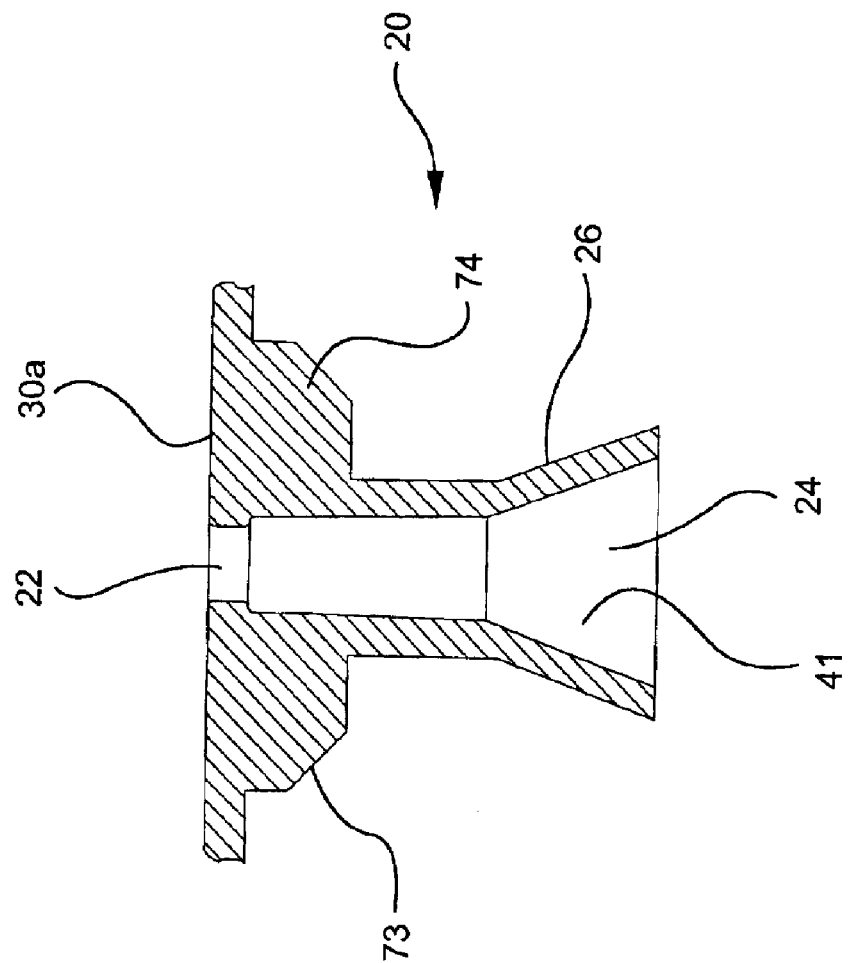

To better engage the base plate, other insert-articles embodiments may include a pilot 74, such as depicted in either FIG. 4C or 8C, to align or register the insert-articles with individual wells in a base plate. FIG. 8C shows a cross-sectional view along line 8A of FIG. 8A, a chamfered boss 73 section of a pilot 74 that is integrally molded, like the flange 30, as part of the insert-article 20. Although each insert-article may possess one, the pilot 74 is located typically beneath the horizontal flange 30, around the upper portion of at least one of the end insert-articles 20.

An advantage that insert-articles have over other tissue culture devices is that inserts are removable from one well plate to another. Cell or tissue samples may be grown in one fluid medium in one plate and transferred in a continuous, high-speed manner into another kind of medium or media in another plate, without physically disturbing the layers of cells on each membrane. This means that cells can be grown in or tested against a series of different media. For instance, cell or tissue samples in insert-articles can be first grown in common fluid medium in a base plate with a common reservoir, and then transferred to individual wells in another base plate. With such an arrangement, the cell samples are grown until confluent and fed uniformly. The nature of tissue culture membranes affixed permanently in well plates slows and detracts from desired high-throughput and automation capabilities. To change growth medium for those kinds of culture devices, fluid from within each well must be changed individually each time a new medium or test fluid is introduced.

A microporous membrane 28, for example as described in U.S. Pat. No. 5,376,273, forms the bottom of each insert-article 20. The permeable membrane serves as a substrate for cell growth and is preferably track etched, such as nucleopore (polycarbonate) or polyethylene terephthalate (PET). Cast membranes of nylon, cellulose acetate, or cellulose nitrate can also be used. The membrane may be corona or plasma treated in order to obtain a hydrophilic surface. Alternatively or in addition, the surface of the well 42 in the base plate may be corona or plasma treated to create a hydrophilic surface and thereby reduce surface tension, which in turn helps to prevent air entrapment. The membrane may be permanently affixed to the bottom opening of an insert-article, or alternatively, the membrane may be detachable. For example, two or more posts extending downward from the bottom edge of the sloping sidewall may secure a membrane to the bottom of the vessel. The posts engage one or more recesses on the edge of a frame that holds the membrane taut.

Figure 9A:
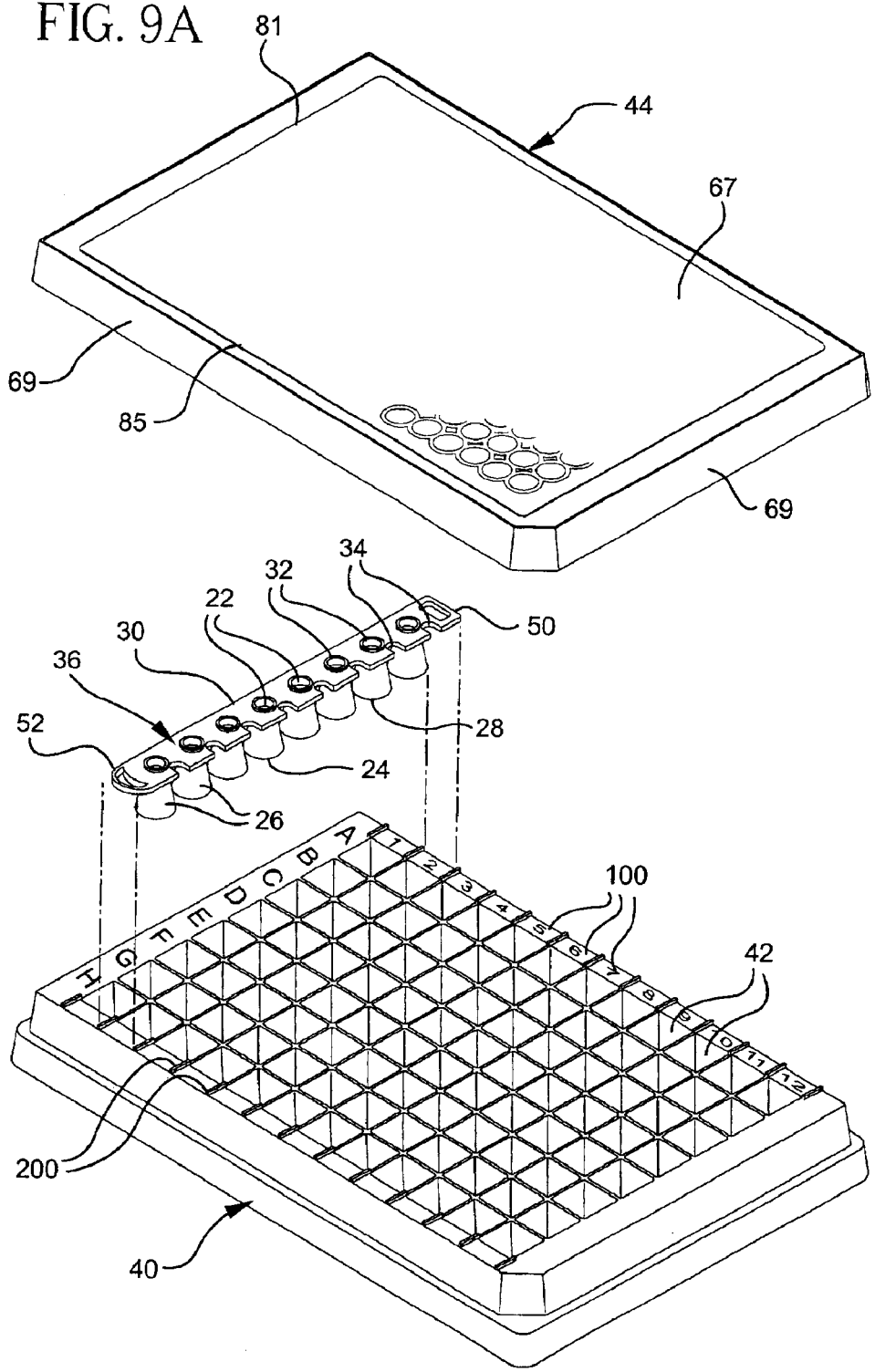
FIG. 9A is an exploded view of an embodiment of the present invention including a 96-well format base plate with enlarged wells, vessels arrayed on detachable strips and a clear plastic cover.
Figure 9B:
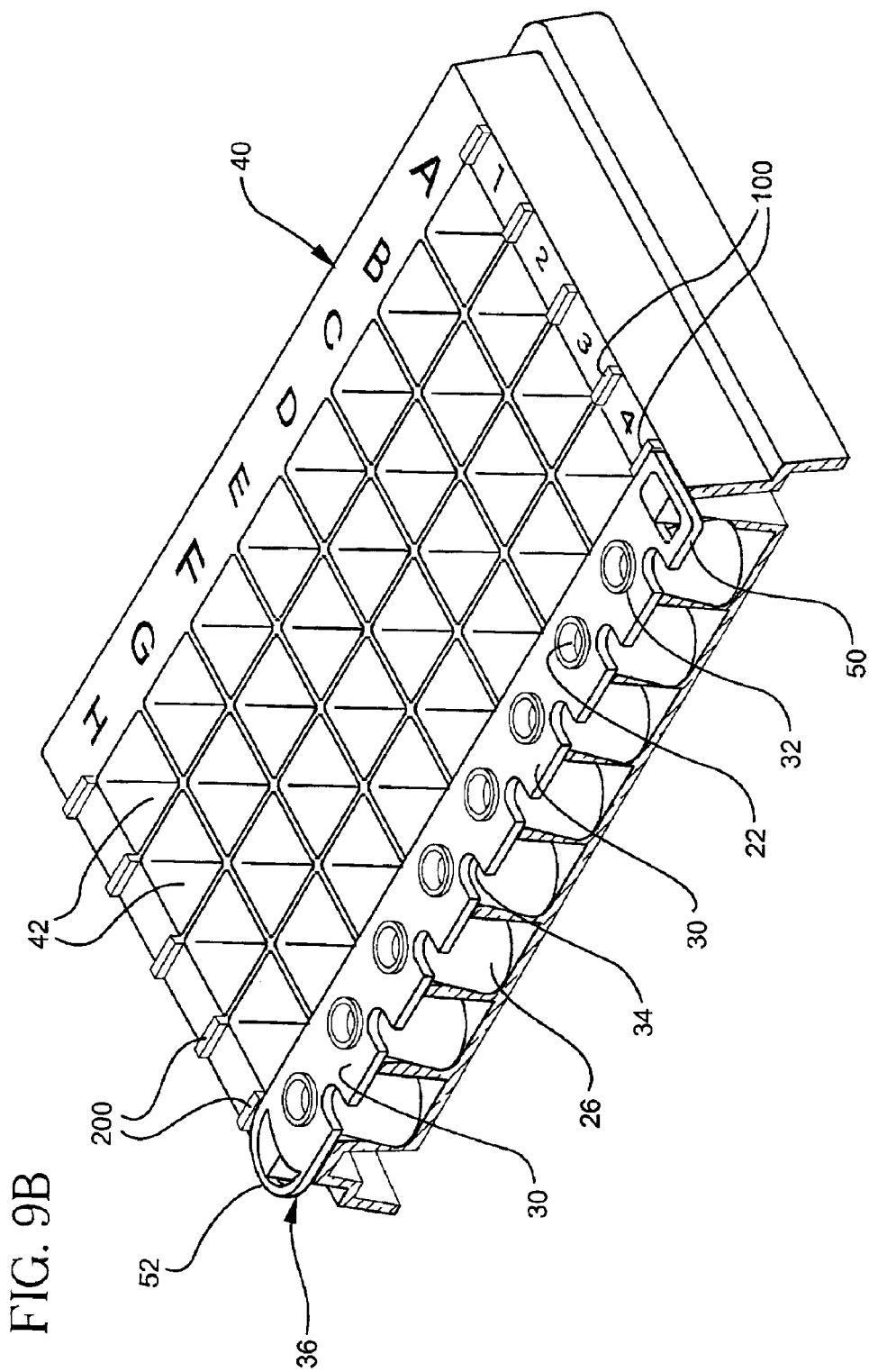
FIG. 9B depicts a detailed view, in perspective and cross-section, of a fragment of FIG. 9A.

FIG. 9A shows an exploded view of an embodiment of the present invention. The embodiment includes a base plate 40 with either standard or enlarged wells 42 and vessels 20 arrayed in detachable strips 36, and a clear plastic cover 44. FIG. 9B depicts a detailed view of a fragment and cross-section of FIG. 9A. The bottom of each individual vessel 20 is suspended by a certain predetermined distance above the bottom of the well 42 beneath. The wells 42 in the multi-well base plate 40 may have a larger well diameters than standard, which permits a membrane 28 with a surface area that is equal to or larger than that used in standardized wells to be inserted. A number of individual strips 36 of 8- or 12-inserts can be arrayed in series one next to another in a 96-well conformation. The general description about base plates with enlarged wells applies equally well to a single-piece unit of 96 insert-articles, which may be more compatible with the existent automated handling and processing robotics. A 96-insert-article unit may be made according to the method described above or, as stated before, with individual multi-insert strips molded together to form a single, large matrix of insert-articles with a standard 96-well footprint. In an embodiment, each of the components is molded preferably of transparent plastic (e.g., polystyrene, polyester, or polypropylene) to permit viewing of the contents of the insert strips and wells or reservoir. Additionally, fluorescent or luminescent assays may be more easily read from below the wells through clear plastic. Alternatively, if a common fluid medium or washing solution is used for all the cultures, the base plate may be configured with a single, large well or reservoir chamber.

In a conventional well plate, illustrated in FIG. 1, the space 16 between wells is taken up by separate sidewalls for each well and a top surface of the plate. This is a waste of space. According to a design, the inter-well space, which was previously not utilized, is incorporated into the volume of the wells of the present base plate. A thinner sidewall of de-minimus thickness, preferably not more than about 0.065 inches, more preferably not exceeding about 0.050 or 0.030 inches, is employed and configured such that adjacent wells share at least one common sidewall. A uniformly thinner sidewall provides a larger volume of space for each well, while it reduces cost of materials and improves the quality of fabrication. The distance between the centerlines of each row, and the centers of adjacent wells in the same row are not affected. The prescribed standard of distance, 0.354 inches, is retained. The diameter of each well can be increased. Thus, the cross-sectional area can be enlarged, for example, doubled from about 0.049 or 0.053 square inches to about 0.098 or 0.16 square inches per well. Actual values will depend on specific sizes and configurations.

Figure 10B:
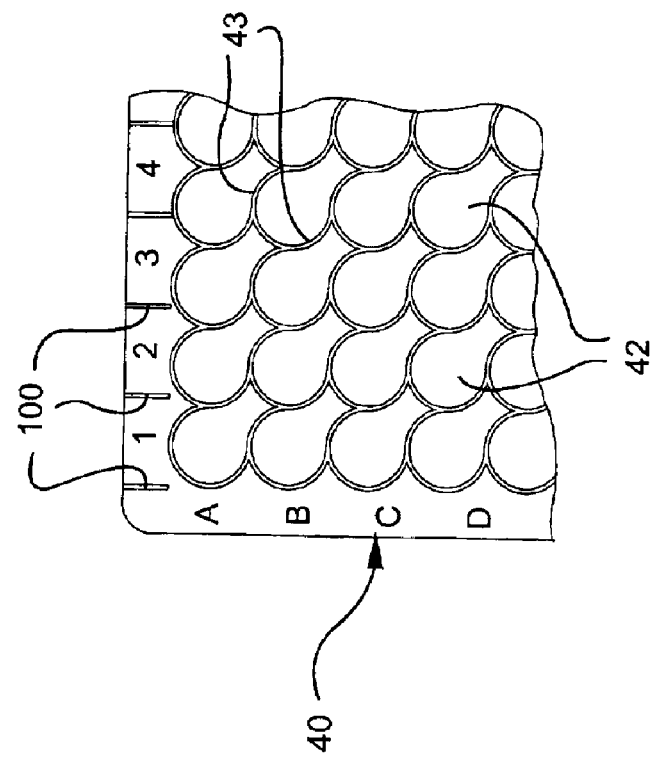
FIGS. 10A and 10B, respectively, depict variations of the shape of enlarged wells in a base plate.
Figure 10A:
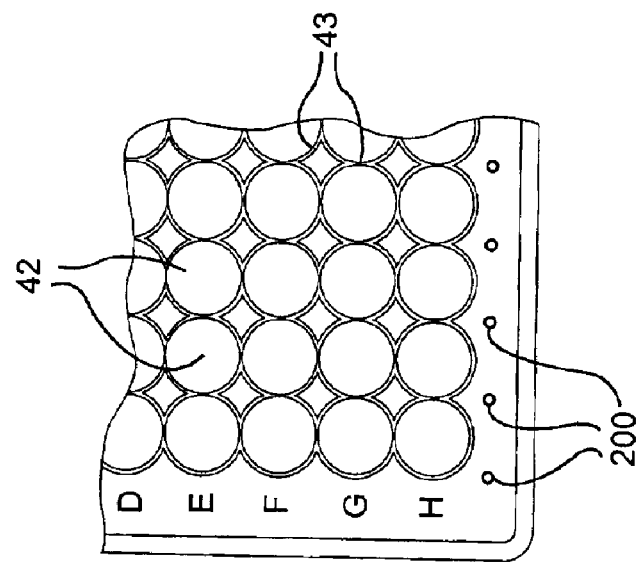

Horizontal cross-sections of a well in the base plate can be circular, square, rectangular, tear or paddle-shaped, or have any other conceivable configuration, such as those illustrated in FIGS. 3A–3E of U.S. Pat. No. 5,972,694, which are included herein. The term "paddle-shaped" shall mean any shape in which a relatively larger cross-sectional area is fluidly connected to a smaller extension of less cross-sectional area. In an embodiment with circular wells, as depicted in FIG. 10A, the sidewall 43 overlaps tangentially with one or more sidewall of adjacent wells 42. In alternate embodiments, which completely maximize the use of the top surface area of the base plate, the wells 42 have either a square or paddle-shaped cross section, as shown in FIGS. 9A and 10B, respectively.

Figure 11A:
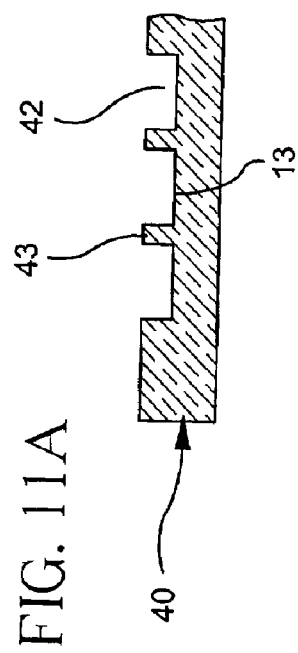
FIGS. 11A, 11B, and 11C, respectively, depict variations for the bottoms of wells.
Figure 11B:
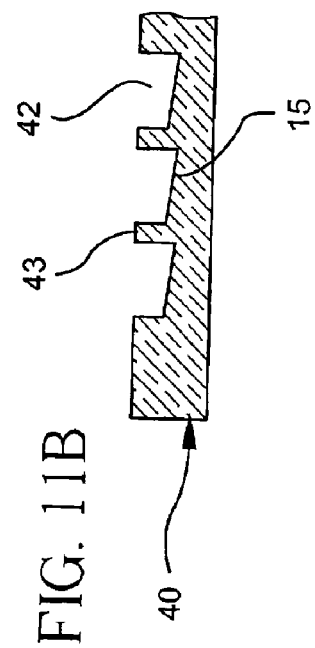

FIGS. 11A through 11B depict different configurations for the bottom wall of wells 42 in a base plate. FIG. 11A shows a well having a flat bottom wall 13, which is parallel to the top surface of the plate. FIG. 11B shows a well with a slanted bottom wall 15.

For many biological studies, it is important to grow a confluent cell monolayer on the membrane substrate. In order to test the degree of confluency of the cell monolayer, electrodes are placed on both sides of the membrane 28 and the electrical resistance across the cell layer and membrane is measured. This is called the trans-epithelial electrical resistance (TEER) value. The well design of the present invention allows for an electrode to be placed into a well in the base plate, through the access aperture, with another electrode placed in the interior cavity 41 of the upper chamber. The electrode to be placed in the well may be curved in such a way as to be positioned directly under the membrane surface. The electrical resistance across the membrane and cell layer can be measured. Alternatively, the base plate can be molded from an electrically conductive polymer or with an electrically conductive surface or coating so that the entire base plate can serve as the bottom electrode for measuring the TEER values across the insert membrane and cell layer. This would require only that probes be introduced into the upper chamber to take TEER measurements.

Figure 11C:
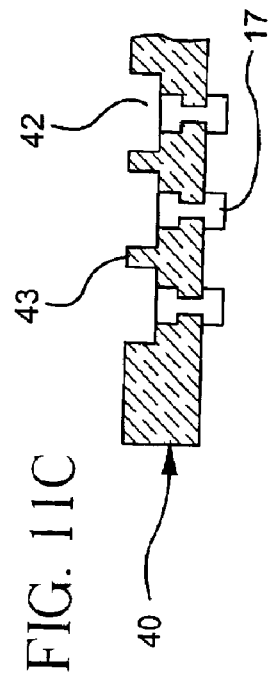

In another embodiment shown in FIG. 11C, a lower electrode 17 is embedded within the bottom wall of the base plate. A conductive contact point permeates the bottom of each well. Alternatively, item 17 may represent a conduit and stopper for either filling or draining fluid culture medium from each well. These last features can increase the efficiency of either monitoring TEER values or changing fluid contents in each well, and make such tasks friendly to automation and high-capacity processing. Lastly, the bottom wall may be either conical for easier drainage or hemispherical for easier fluid collection.

FIGS. 3A and 3B, 4A–4C, and 8A–8C, respectively, each illustrates an example of a strip 36 of insert-articles 20. The horizontal flange 30 at the top of each insert-article may be molded as one continuous piece, joining together individual insert-articles into the multi-insert strip, which may be inserted as a unit into a column of wells in the base plate. The strip of FIGS. 3A and 3B include circular openings 22 define by collar-lips 32 and have access apertures 34. The shape of the collar-lip is not limiting, such that it also can be square or polygonal. The horizontal flange 30 maintains the insert-articles in a flat, linear array with all the bottom surfaces of the wells in a single plane. Therefore, even when a multi-insert strip 36 is removed from the base plate 40, the strip remains a rigid member, which can be easily grasped and handled without bending or warping. Since the bottom surfaces of all the wells are held in one plane, optical measurements can be made readily on a row of wells. In certain embodiments, the horizontal flange 30 has a width of at least 0.350 inches, where the center of a well is at least 0.175 inches from the longitudinal edge 35. The continuous horizontal flange 30 for an eight-insert-article strip has a total length of not less than about 3.208 inches, or sufficient to span the width of a base plate with a standard footprint. Preferably, the distance between the centers of each well or of two access apertures next to one another conforms to the prescribed dimension of a standard 96-well plate of approximately 0.354 inches. Like the strip of wells described in U.S. Pat. Nos. 5, 084, 246 and 5,922,289, the contents of which are incorporated herein by reference, a strip of insert-articles according to the present invention may be placed into a base plate.

According to an embodiment illustrated in FIG. 9A, alpha-numeric characters may be arranged on the horizontal, top surface of the base plate, as coordinates for the rows and columns of an array of wells. A plurality of dissimilar placement members (e.g., ribs, pins, or posts) for aligning and securing multi-insert strips to the base plate is located on the horizontal, top surface of the base plate, around the periphery of the well matrix. Mating members on opposing ends of a multi-insert strip may fit into the space or notch defined by the ribs 100. Depending on the style and configuration of the mating members, a strip 36 can be oriented in a predetermined fashion when inserted into the base plate 40. For example, as pictured in FIGS. 3A and 9A, a multi-vessel strip 36 has dissimilarly shaped flanges 50, 52 at opposing ends. Each flange engages with one of the dissimilar support means (e.g., ribs 100 or pins 200, respectively) on the base plate. The opposing flanges are in this instance a rectangular flange 50, which fits between the ribs 100 on the base plate, and a rounded flange 52 on the opposing end that fits between the pins 200 on the base plate. A virtue of this type of orientation is that, even if the strip 36 is removed from the base plate 1, the dissimilar shapes of the end flanges 50, 52 can aid in visually orienting the multi-vessel strip 36. No ambiguity will exist as to which end of the strip was in the first row A and which end was in the last row H. In some embodiments, the engaging flange at one end of a strip may have an opening or recess in the flange to accommodate the numeric characters 23, which denote each column of wells on the base plate. A pilot 74 may be provided adjacent to each of the terminal inserts at the ends of the multi-vessel strip 36 for a pressure fit against the base plate.

The multi-well base plate may also have a cover 44, like that of FIG. 9A, to protect the contents of each well or culture vessel from evaporation or contamination. The cover includes a horizontal top wall 67 having a downwardly extending peripheral flange 69 molded from transparent plastic (e.g., polystyrene or polypropylene). The upper surface of the top wall has a raised peripheral ridge 81 defining a groove 85, for stacking another base plate on the cover.

The present invention has been described in detail by way of examples. Persons skilled in the art, however, can appreciate that modifications and variations may be made to the present apparatus without departing from the scope of the invention, as defined by the appended claims and their equivalents.

We claim:

1. An apparatus comprising: a plate having a top surface and a number of well components; said well components each having a lower portion and an upper portion; said lower portion having at least one chamber, said upper portion having at least one vessel and an access port; said vessel having at least one sidewall defining a top opening and a bottom opening, each of predetermined cross-sectional area, wherein an inner cross-sectional area, between said top and bottom openings, in a horizontal plane orthogonal to a sidewall of said chamber, is smaller than the inner cross-sectional area of said bottom opening, and said vessel is sized to fit into said chamber, said top opening and said access port provided in said top surface, said access port providing communication between said top surface and said chamber; said bottom opening capable of binding with a membrane.

2. The apparatus according to claim 1, wherein said upper portion comprises a matrix of individual vessels.

3. The apparatus according to claim 1, wherein said chamber has a bottom wall.

4. A plate for use as an upper portion of a biological assay plate, the plate comprising: a top surface having a number of vessels; each of said vessels having a central cavity, defined by a sidewall, extending from a first open end to a second open end, wherein said second open end has an inner cross-sectional area greater than the inner cross-sectional area of said first open end or wherein said second open end has an inner cross-sectional area greater than a cross-sectional area in a horizontal plane between said first and second open ends; said second open end capable of binding with a permeable substrate; and said top surface having access portals wherein said access portal forms part of said first open end and provides access to a volume in the assay plate external to the vessel.

5. The plate according to claim 4, wherein at least one access portal is associated with each vessel.

6. The plate according to claim 4, wherein a recess is formed in said sidewall adjacent to said access portal.

7. An apparatus for biological cultures, the apparatus comprising: an upper plate having a number of upper chambers, each of said upper chambers defined by a sidewall, extending from a top open end to a bottom open end, wherein said bottom open end has an inner cross-sectional area greater than either the inner cross-sectional area of said top open end or wherein said second open end has an inner cross-sectional area greater than a cross-sectional area in a horizontal plane between said top and second open ends; a membrane covering said bottom open end, which forms the bottom of each of said upper chambers; and a lower plate having a number of wells, each well having a bottom and at least one sidewall wherein said bottom open end extends into said well.

8. The apparatus according to claim 7, wherein each upper chamber in said upper plate further has an associated access portal providing communication with at least one well in said lower plate.

9. The apparatus according to claim 7, wherein said upper plate further comprises a matrix of said upper chambers corresponding to a matrix of wells.

10. The apparatus according to claim 9, wherein said matrix of upper chambers corresponds to a 96-well format.

11. The apparatus according to claim 9, wherein said matrix of upper chambers corresponds to a 192-well format.

12. The apparatus according to claim 9, wherein said matrix of upper chambers corresponds to a 384-well format.

13. The apparatus according to claim 7, wherein said upper plate further comprises a strip of upper chambers.

14. The apparatus according to claim 13, wherein said strip of upper chambers is an 8 or 12 upper chamber strip.

15. The apparatus according to claim 7, wherein said lower plate has a plurality of tear or paddle-shaped wells.

16. The apparatus according to claim 7, wherein the lower plate further comprises: dissimilar engagement mechanisms on two opposing sides of the lower plate for aligning and securing a multi-upper-chamber strip, such that each upper chamber is suspended in a corresponding well a predetermined distance above the bottom of said well.

17. The apparatus according to claim 7, wherein said wells have a larger cross-sectional area than industry-standard wells.

18. The apparatus according to claim 7, wherein said lower plate further includes a matrix of wells arrayed to correspond to a 96-well format.

19. The apparatus according to claim 18, wherein said lower plate further includes a matrix of wells arrayed to correspond to a 384-well format.

20. The apparatus according to claim 7, wherein the wells are hydrophilic.

21. The apparatus according to claim 7, wherein the wells are hydrophobic.

22. The apparatus according to claim 7, wherein said bottom wall of said wells has an electrode integrated therein.

23. The apparatus according to claim 7, wherein the horizontal cross-sectional area of said wells has a rectilinear form.

24. The apparatus according to claim 7, wherein said bottom wall of said well is slanted.

25. The apparatus according to claim 7, wherein said bottom wall of said well is conical or hemispherical in shape.

26. The apparatus according to claim 7, wherein said bottom wall of said well is parallel to a horizontal top surface.

27. The apparatus according to claim 7, wherein said apparatus is molded from either an electrically conductive polymer or a polymer coated with electrically conductive material.

28. The apparatus according to claim 7, wherein said upper chamber further comprises: a collar-lip around said top open end of each vessel, and a sloped sidewall extending downward and outward from said top open end.

29. The apparatus according to claim 7, wherein an array of said upper chamber has at least one upper chamber with a pilot for registering said array with said lower plate.

30. An apparatus comprising: a plurality of multi-insert strips, each comprising at least two vessels, each vessel having a sidewall defining a top and bottom opening, each of a predetermined cross-sectional area, wherein said bottom opening has an inner cross-sectional area greater than the inner cross-sectional area of either said top opening or wherein said second open end has an inner cross-sectional area greater than a cross-sectional area in a horizontal plane between said top and bottom openings; a base plate having a number of wells, each with a bottom wall and at least one sidewall, said base plate having support mechanisms on two opposing sides of for securing said multi-insert strip to said base plate such that said bottom opening extends into the well; and said bottom opening capable of engaging with a permeable substrate.

31. The apparatus according to claim 30, wherein at opposing ends of said multi-insert strip are located flanges for aligning and securing the strip.

32. The apparatus according to claim 31, wherein said alignment flanges are dissimilar from one another in a predetermined orientation relative to the base plate.

33. The apparatus according to claim 30, wherein an arrangement of a number of said multi-insert strips further constitutes a matrix of inserts conforming to a 96-well or 384-well format.

34. The apparatus according to claim 30, such that at least a part of each insert has a downwardly flared shape.

* * * * *